US011850357B2

(12) United States Patent
Hilliard et al.

(10) Patent No.: US 11,850,357 B2
(45) Date of Patent: Dec. 26, 2023

(54) PORTABLE HALOTHERAPY DEVICE FOR AEROSOLIZING SALT

(71) Applicant: INFINITY SALT AIR MACHINE, LLC, Charlotte, NC (US)

(72) Inventors: Aubrey L. Hilliard, Charlotte, NC (US); Anne R Glasgow, Charlotte, NC (US)

(73) Assignee: Infinity Salt Air Machine, LLC, Charlotte, NC (US)

(*) Notice: Subject to any disclaimer, the term of this patent is extended or adjusted under 35 U.S.C. 154(b) by 582 days.

(21) Appl. No.: 17/107,141

(22) Filed: Nov. 30, 2020

(65) Prior Publication Data

US 2021/0077756 A1   Mar. 18, 2021

Related U.S. Application Data

(63) Continuation of application No. PCT/US2019/061327, filed on Nov. 13, 2019.
(Continued)

(51) Int. Cl.
*A61M 15/02* (2006.01)
*A61M 16/00* (2006.01)

(52) U.S. Cl.
CPC ........ *A61M 15/02* (2013.01); *A61M 16/0066* (2013.01); *A61M 2202/066* (2013.01); *A61M 2206/16* (2013.01)

(58) Field of Classification Search
CPC .... A61M 11/002; A61M 11/02; A61M 15/02; A61M 16/0066; A61M 2202/066;
(Continued)

(56) References Cited

U.S. PATENT DOCUMENTS 2,021,281 A   11/1935   Bingman
2,582,547 A   1/1952   Kronstad
(Continued)

FOREIGN PATENT DOCUMENTS

WO   2020102455 A1   5/2020

OTHER PUBLICATIONS

"International Search Report" and "Written Opinion of the International Search Authority" (ISA/US) in Infinity Salt Air Machine, LLC, International Patent Application Serial No. PCT/US2019/061327, dated Feb. 12, 2020 (6 pages).

*Primary Examiner* — Joshua Lee
(74) *Attorney, Agent, or Firm* — Tillman, Wright & Wolgin; James D. Wright; David R. Higgins

(57) ABSTRACT

A portable halotherapy device includes a housing, a grinding chamber with a grinding blade that breaks apart dry granular salt into salt particles small enough for halotherapy, an air duct routing air to the chamber, a fluid conduit, and a high-speed exhaust fan. Ambient air flows through the air ducts into the grinding chamber to produce a first air current. Air is diverted from the first air current upward, in a second air current, through the fluid conduit and the fan. The first air current helps move dry granular salt around and against the grinding chamber, breaking it into small salt particles. The second air current is arranged relative to the first air current such that small salt particles, but not larger pieces, are carried as salt aerosol upward through the fluid conduit and fan for distribution to the environment, thereby facilitating a halotherapy session.

20 Claims, 13 Drawing Sheets

Related U.S. Application Data

(60) Provisional application No. 62/760,681, filed on Nov. 13, 2018.

(58) Field of Classification Search
CPC ........ A61M 2205/07; A61M 2205/502; A61M 2205/8206; A61M 2206/16
See application file for complete search history.

(56) References Cited

U.S. PATENT DOCUMENTS

| | | | |
|---|---|---|---|
| 5,881,720 A * | 3/1999 | Vinogradov | A61P 11/00 128/200.14 |
| 6,651,654 B2 * | 11/2003 | Rogacki | A61M 15/00 482/13 |
| 8,662,078 B2 * | 3/2014 | Zoltan | A61M 11/003 128/203.15 |
| 9,629,968 B2 * | 4/2017 | Monterenzi | A61M 15/00 |
| 9,764,103 B2 * | 9/2017 | Neff | A61M 15/0091 |
| 10,583,261 B2 * | 3/2020 | Ohrt | A61M 15/0003 |
| 10,624,813 B2 * | 4/2020 | Monterenzi | A61M 35/30 |
| 2008/0163871 A1 | 7/2008 | Bozoky et al. | |
| 2012/0126043 A1 * | 5/2012 | Viherlahti | A61P 11/10 241/38 |
| 2012/0247463 A1 * | 10/2012 | Zoltan | A61M 15/0025 128/203.15 |
| 2013/0125888 A1 * | 5/2013 | Monterenzi | A61M 15/00 128/203.15 |
| 2017/0072150 A1 * | 3/2017 | Lankau | A61M 15/0085 |
| 2017/0246080 A1 * | 8/2017 | Monterenzi | A61M 15/02 |
| 2018/0021527 A1 * | 1/2018 | Kokai | A61M 15/0006 128/200.17 |
| 2019/0083395 A1 * | 3/2019 | Doshi | A61K 9/0078 |
| 2021/0205549 A1 * | 7/2021 | Kokai | A61M 15/02 |

* cited by examiner

PORTABLE HALOTHERAPY DEVICE FOR AEROSOLIZING SALT

CROSS-REFERENCE TO RELATED APPLICATION

The present application is a U.S. continuation patent application of, and claims priority under 35 U.S.C. § 120 to, International Application No. PCT/US2019/061327, filed Nov. 13, 2019, designating the U.S., and entitled "PORTABLE HALOTHERAPY DEVICE FOR AEROSOLIZING SALT," which '327 application published as WO 2020/102455 on May 22, 2020, which '327 application and the application publication thereof are each incorporated herein by reference in their entirety, and which '327 application, for purposes of the United States, is a U.S. nonprovisional patent application of, and claims priority under 35 U.S.C. § 119(e) to, U.S. provisional patent application Ser. No. 62/760,681, filed Nov. 13, 2018, and entitled, "APPARATUS FOR AEROSOLIZING SALT," which '681 application is incorporated by reference herein in its entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention is directed to salt aerosolizers, and, in particular, to compact, portable salt aerosolizers that grind, filter, and distribute salt in aerosolized form for convenient and inexpensive halotherapy sessions.

Background

Halotherapy is a well-known form of alternative medicine making use of salt. Halotherapy has developed over many millennia. There are records dating to the twelfth century of spa resorts in which patrons bathe in mineral waters. In the mid 1800's, Polish physicians noticed that salt miners rarely suffered from respiratory diseases. Later, it was observed that many asthma and allergy sufferers who hid out in the salt mines during the war emerged breathing freely. From these observations, speleotherapy (salt cave therapy) was founded.

Halotherapy has been credited for detoxifying properties and a wide range of health benefits to halotherapy. Salt's well known drying effect may help to clean up bronchial secretions. Many have reported improvement in symptoms of chronic obstructive pulmonary disease following halotherapy. Inhalation of hypertonic saline can stimulate bronchoconstriction, which may be used in the diagnosis or evaluation of asthma symptoms. Spa owners sometimes attribute detoxifying properties and a wide range of health benefits to halotherapy. The healthcare systems in many countries pay for people to spend several weeks per year in salt mines in order to prevent heal respiratory and skin conditions. Athletes throughout the world incorporate salt therapy sessions in their training regimens and it increases oxygenation and endurance.

In view of these possible benefits, halotherapy rooms, built to recreate the salt cave environment, are now found around the world. Of course, salt mines are neither convenient nor readily accessible for most people. Thus, special equipment called halogenerators have been developed to grind and disperse salt aerosol into the air. One such 45 minute halotherapy session has been said to be the equivalent of three days in the salt caves. Many hospitals in Russia treat their respiratory patients in halotherapy rooms.

Unfortunately, while useful, dedicated halotherapy rooms are expensive to build and require specialized equipment to be installed therein. Furthermore, many people currently do not have ready access to such a room, or have the time to travel to such a room or complete a session. Thus, a need exists for a compact halotherapy device for use at home in short sessions to facilitate inexpensive halotherapy anytime or anywhere a user wishes.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

The present invention includes many aspects and features. Moreover, while many aspects and features relate to, and are described in, the context of portable devices for aerosolizing salt for halotherapy, the present invention is not limited only to such use, as will become apparent from the following summaries and detailed descriptions of aspects, features, and one or more embodiments of the present invention Broadly defined, the present invention according to one aspect relates to a portable halotherapy device, including: one or more housings that may be coupled together to define a single operational unit; a grinding chamber, having an interior with a moving grinding blade therein, that is disposed within the one or more housings and that breaks apart dry granular salt in the interior thereof into salt particles small enough to be used for halotherapy; an air intake assembly, including one or more air ducts that each route ambient air from outside the one or more housings into the interior of the grinding chamber; a fluid conduit that is disposed within the one or more housings and that has an inlet at a first end and an outlet at a second end, wherein the conduit extends upward from the first end, wherein the inlet is in fluid communication with the interior of the grinding chamber; and an exhaust unit, the exhaust unit including a high-speed fan disposed within the one or more housings at the second end of the fluid conduit and in communication with the outlet thereof; wherein the moving grinding blade and the high-speed fan together operate to produce an airflow pattern that causes ambient air to be brought through the air ducts of the air intake assembly and into the grinding chamber where a regular and predictable first air current is produced, wherein the airflow pattern further causes air to divert from the first air current upward, in a second air current, into the inlet of the fluid conduit and through the high-speed fan of the exhaust unit for distribution to the outside of the one or more housings; and wherein the first air current assists in moving the dry granular salt around the grinding chamber and against surfaces thereof, thereby assisting in breaking apart the dry granular salt into small salt particles for halotherapy, while the second air current is arranged relative to the first air current such that the small salt particles, but not larger pieces of salt, are carried in the form of a salt aerosol by the second air current upward into the inlet of the fluid conduit and through the high-speed fan of the exhaust unit for distribution to the outside of the one or more housings, thereby facilitating a halotherapy session.

In a feature of this aspect, the one or more housings include a bottom unit and a top unit, wherein the grinding chamber is disposed in the bottom unit, and wherein the exhaust unit is disposed at the top of the top unit. In further features, the top unit is removably coupled to the bottom unit; the top unit is removably coupled to the bottom unit via magnets; electrical connections are made between the top unit and the bottom unit via spring-loaded electrical contacts; removal of the top unit from the bottom unit exposes the interior of the grinding chamber for loading with dry granular salt and for removal of salt residue; the one or more air ducts are formed from a combination of first surfaces and/or structures on a bottom wall of the top unit and second surfaces and/or structures on a top wall of the bottom unit such that the air ducts are only established when the top unit is coupled to the bottom unit; the bottom wall of the top unit includes a surface and/or structure serving as a ceiling of each of the one or more air ducts, and the top wall of the bottom unit includes a surface and/or structure serving as a floor of each of the one or more air ducts; the exhaust unit includes a separate housing that is removably coupled to the top of the top unit; the exhaust unit is removably coupled to the top of the top unit via magnets; electrical connections are made between the exhaust unit and the top of the top unit via spring-loaded electrical contacts; and/or removal of the exhaust unit from the top of the top unit exposes upper portions of the fluid conduit and the high speed fan for removal of salt residue.

In another feature of this aspect, the first end of the fluid conduit extends downward into the interior of the grinding chamber. In further features, the fluid conduit is funnel-shaped with the first end thereof being narrow and the second end thereof being substantially wider than the first end; the fan has an inlet side and an outlet side, and the substantially wider second fan is disposed against and surrounding the inlet side of the fan such that substantially all of the salt aerosol passing up through the funnel-shaped conduit passes into and through the fan; the fan is driven at a rotational speed of at least 2500 rpm; the fan is driven at a rotational speed of at least 4000 rpm; the fan is driven at a rotational speed of approximately 5000 rpm; the exhaust unit includes an exhaust grille to whose underside the fan unit is attached; the fluid conduit defines a first axis, and the first axis extends downward through a geometric center of the grinding chamber; the high-speed fan of the exhaust unit rotates around a second axis, and the first and second axes are collinear; the grinding blade rotates around a third axis, and wherein the first and third axes are collinear; the grinding chamber is cylindrical and defines a fourth axis, and the first and fourth axes are collinear; the horizontal cross-section of the fluid conduit is circular through its length; the fluid conduit extends into the grinding chamber a distance of at least 20% of the interior height of the grinding chamber; and/or the fluid conduit extends into the grinding chamber a distance of at least 33% of the interior height of the grinding chamber.

In another feature of this aspect, the moving grinding blade is disposed at a bottom of the interior thereof and rotates in a first rotational direction about a first axis. In further features, the grinding blade includes one or more downwardly-angled vanes or fins such that the blade pushes air downward and in the first rotational direction as the blade rotates; rotation of the grinding blade in the first rotational direction serves to pull the ambient air in through the air ducts of the air intake assembly and down toward the bottom of the grinding chamber where it swirls around the bottom in the first rotational direction, thereby defining the first air current; each of the one or more air ducts has an inlet and an outlet, and each outlet is disposed at a top of the grinding chamber such that the ambient air brought through the air ducts is introduced to the grinding chamber at the top thereof before being pulled down toward the bottom thereof by the grinding blade; each of the one or more air ducts takes the form of a spiral arm that spirals out from the first axis such that ambient air passing therethrough enters the grinding chamber in a direction tangential to the grinding chamber and in a rotational direction that is the same as the first rotational direction; the air intake assembly includes exactly three air ducts in the form of three spiral arms; each of the one or more air ducts has a width that tapers inwardly from the inlet to the outlet thereof; each of the one or more air ducts has a height that tapers inwardly from the inlet to the outlet thereof; the grinding blade is driven at a rotational speed of at least 5000 rpm; the grinding blade is driven at a rotational speed of at least 7500 rpm; and/or the grinding blade is driven at a rotational speed of approximately 8700 rpm.

In another feature of this aspect, the first air current flows from outside the one or more housings through the one or more air ducts into the grinding chamber and swirls in a downward and high-speed circular direction around the periphery thereof where the first air current interacts with the dry granular salt and the salt particles as such particles are created, and the second air current flows directly upward at or near a geometric center of the grinding cylinder and into the inlet of the fluid conduit, carrying the resulting salt aerosol up through the fluid conduit and through the high speed fan for distribution to the outside.

In another feature of this aspect, the portable halotherapy device further includes an electrical subsystem. In further features, the electrical subsystem operates the fan in the exhaust unit independently from the grinding blade; the electrical subsystem controls the fan to operate continuously but controls the grinding blade to operate only intermittently; in at least one mode of operation, the electrical subsystem controls the fan to operate continuously for a predetermined period of time in order to limit an amount of salt aerosol that is distributed from the device but controls the grinding blade to operate only intermittently during the predetermined period of time; the predetermined time is between approximately 5 minutes and 30 minutes, inclusive; the predetermined time is between approximately 10 minutes and 20 minutes, inclusive; the electrical subsystem includes a user interface; the user interface includes a start button or other control for initiating operation, and wherein the electrical subsystem controls the fan to operate continuously for the predetermined period of time, while controlling the grinding blade to operate only intermittently during the predetermined period of time, in response to the start button or other control being activated; the user interface includes at least one mode button or other control for selecting a particular mode of operation, and the predetermined period of time depends on the particular mode of operation that is selected; and/or in one particular mode of operation, the predetermined period of time is approximately 10 minutes, and in another particular mode of operation, the predetermined period of time is approximately 20 minutes.

In another feature of this aspect, the small particles are substantially all less than 15 microns in diameter. In further features, the small particles are substantially all less than 10 microns in diameter; and/or at least 80% of the small particles are approximately 5 microns or less in diameter.

In another feature of this aspect, the small salt particles are carried via the second air current at a rate of at least 10 cfm. In further features, the small salt particles are carried via the second air current at a rate of at least 20 cfm; and/or the small salt particles are carried via the second air current at a rate in the range of approximately 25 cfm to 30 cfm.

Broadly defined, the present invention according to one aspect relates to a method of producing and distributing a salt aerosol from a portable halotherapy for a halotherapy session, including: drawing ambient air through an air intake assembly, including one or more air ducts; routing the ambient air into a grinding chamber having an interior with a moving grinding blade therein; with the grinding blade, breaking apart dry granular salt contained in the interior thereof into salt particles small enough to be used for halotherapy; with an exhaust unit, including a high-speed fan, drawing air up into an inlet at a first end of a fluid conduit and through the conduit to a second end where the high-speed fan is located, wherein the conduit extends upward from the first end, wherein the inlet is in fluid communication with the interior of the grinding chamber; with the moving grinding blade and the high-speed fan together, producing an airflow pattern that causes ambient air to be brought through the air ducts of the air intake assembly and into the grinding chamber where a regular and predictable first air current is produced, and that further causes air to divert from the first air current upward, in a second air current, into the inlet of the fluid conduit and through the high-speed fan; with the first air current, assisting the grinding blade in moving the dry granular salt around the grinding chamber and against surfaces thereof, thereby assisting in breaking apart the dry granular salt into small salt particles for halotherapy; with the second air current, carrying the small salt particles, but not larger pieces of salt, are carried in the form of a salt aerosol upward into the inlet of the fluid conduit and through the high-speed fan of the exhaust unit; and distributing the salt aerosol to an environment, thereby facilitating a halotherapy session.

In a feature of this aspect, the small salt particles are carried via the second air current at a rate of at least 10 cfm. In further features, the small salt particles are carried via the second air current at a rate of at least 20 cfm; and/or the small salt particles are carried via the second air current at a rate in the range of approximately 25 cfm to 30 cfm.

Further areas of applicability of the present invention will become apparent from the detailed description provided hereinafter. It should be understood that the detailed description and specific examples, while indicating preferred embodiment(s) of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
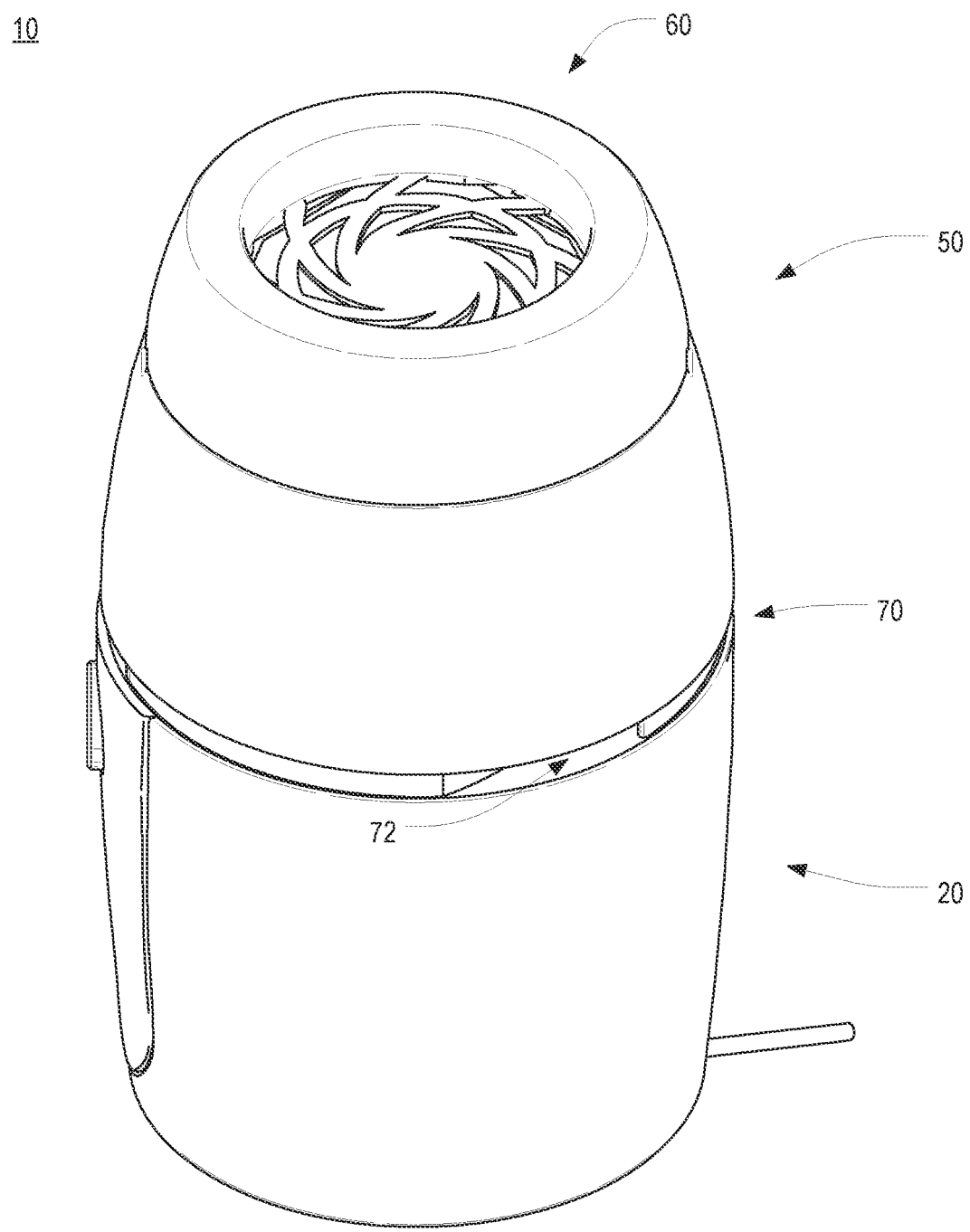
FIG. 1 is a side orthogonal view of a compact halotherapy device in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Furthermore, an embodiment of the invention may incorporate only one or a plurality of the aspects of the invention disclosed herein; only one or a plurality of the features disclosed herein; or combination thereof. Moreover, many embodiments, including adaptations, variations, modifications, and equivalent arrangements, are implicitly disclosed herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Further, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiments is merely exemplary in nature and is in no way intended to limit the invention, its implementations, or uses.

Figure 2:
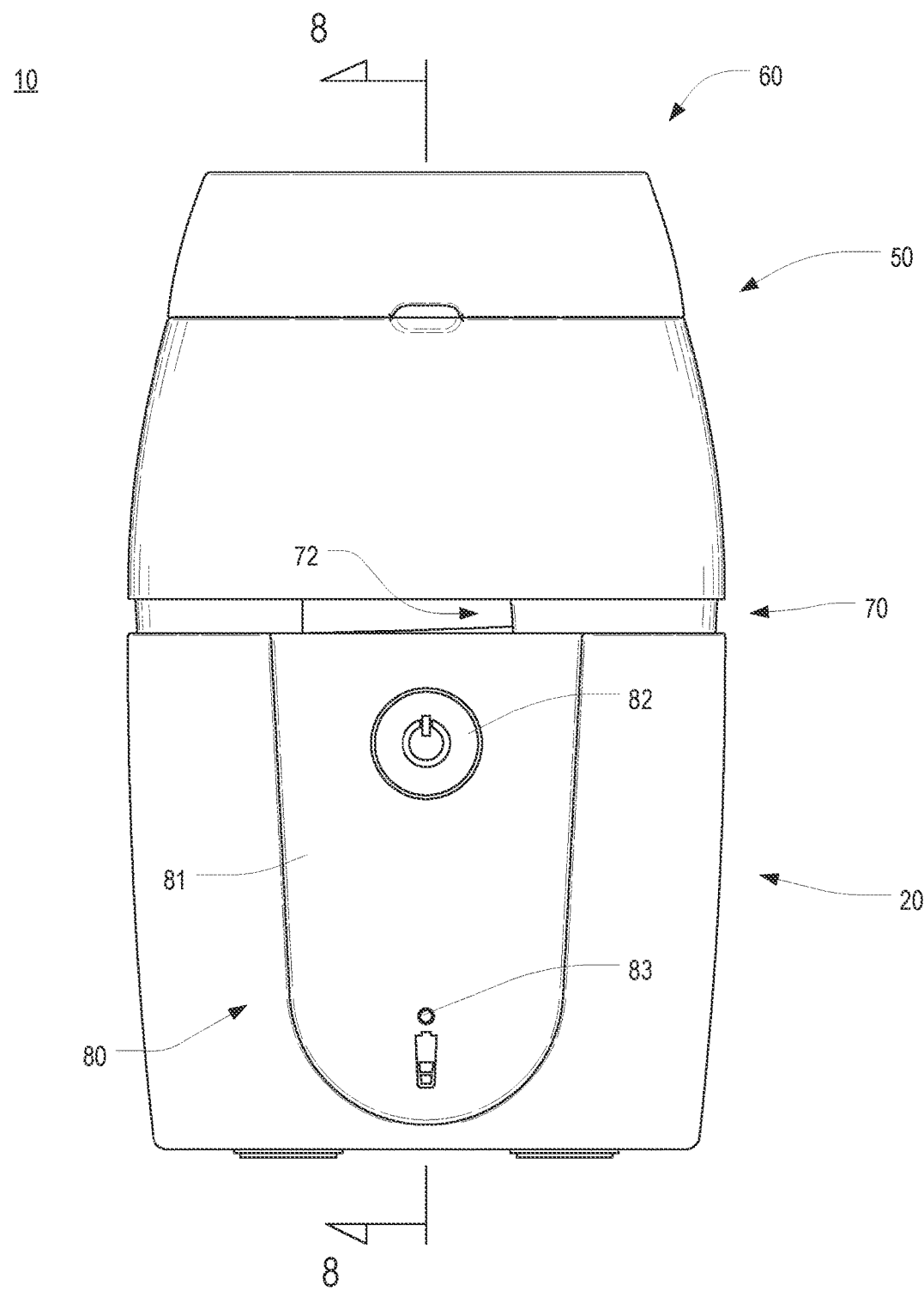
FIG. 2 is a front view of the halotherapy device of FIG. 1.
Figure 3:
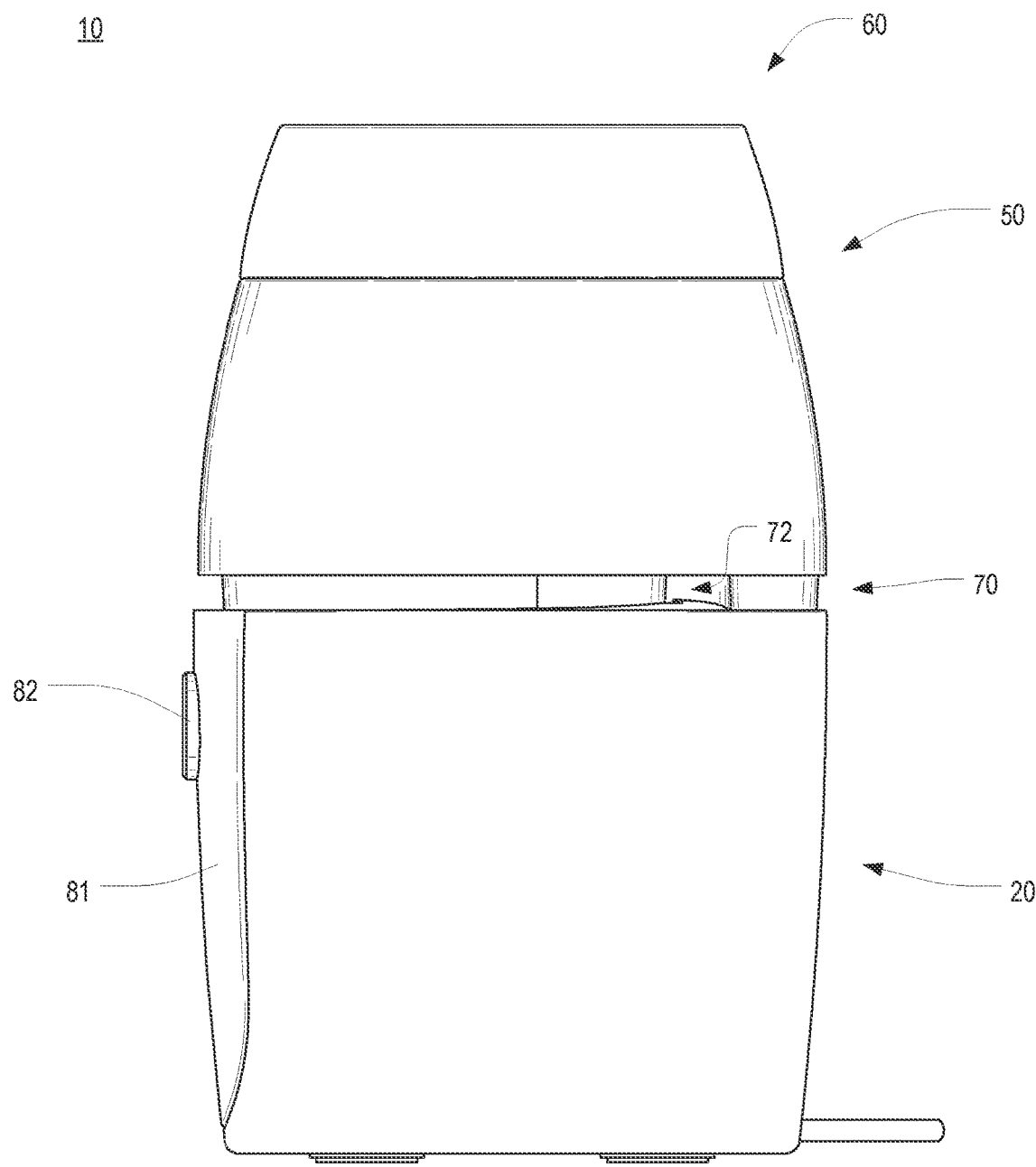
FIG. 3 is a right side view of the halotherapy device of FIG. 1.

FIG. 1 is a side orthogonal view of a compact halotherapy device 10 in accordance with one or more preferred embodiments of the present invention, while FIGS. 2 and 3 are a front view and a right side view, respectively, of the halotherapy device of FIG. 1. The halotherapy device 10 includes a bottom unit 20 and a top unit 50 with an air intake assembly 70 established at the junction between the top and bottom units 50,20. As described further herein, the air intake assembly 70 routes ambient air into the bottom unit 20, which functions primarily as a pulverizing and filtering unit. The top unit 50 functions primarily as a distribution unit, drawing salt aerosol from the bottom unit upward and exhausting it into the room in which the device 10 is operated. These components and their operation are described in detail hereinbelow.

Figure 4:
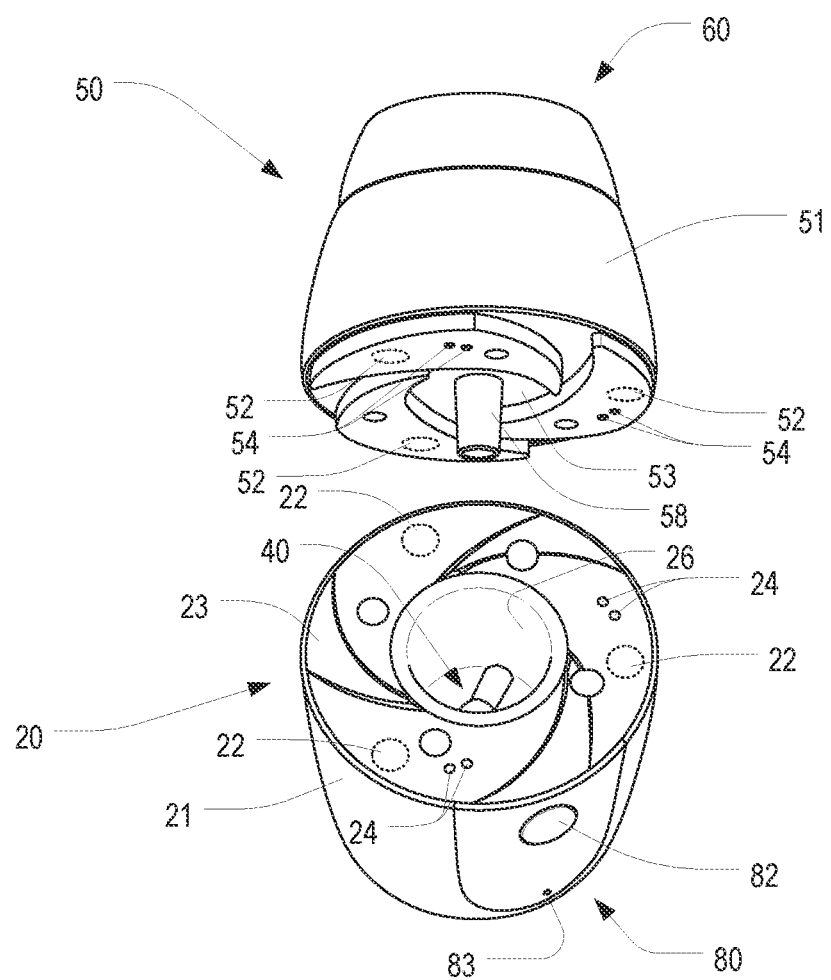
FIG. 4 is a perspective view of the halotherapy device of FIG. 1, shown with the top and bottom units separated from one another.
Figure 5:
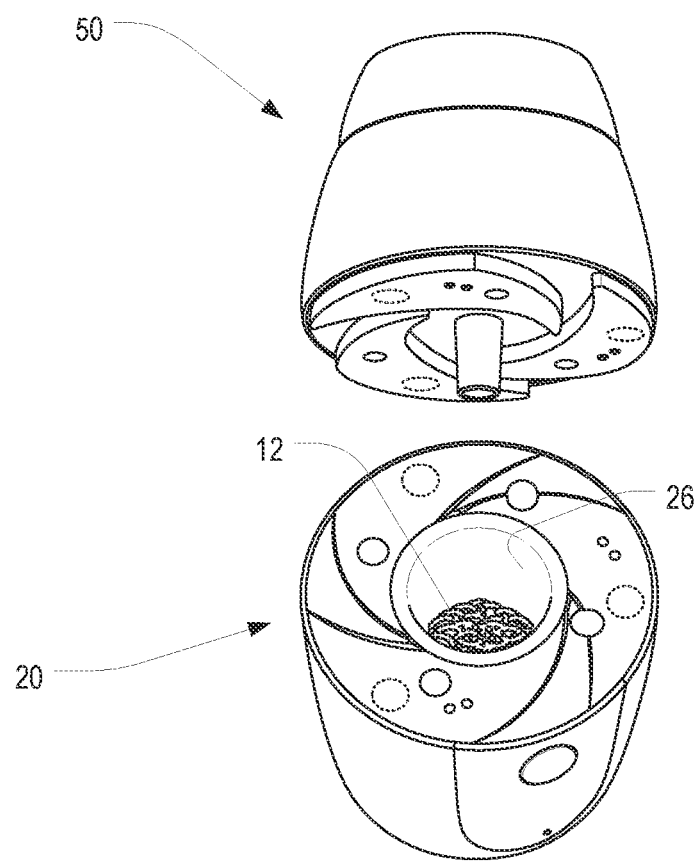
FIG. 5 is a similar view showing a quantity of salt loaded into the bottom unit.

The top and bottom units 50,20 are designed to be removably coupled together to permit salt 12 to be loaded into the bottom unit 20 as well as to facilitate cleaning and other functions. In this regard, FIG. 4 is a perspective view of the halotherapy device of FIG. 1, shown with the top and bottom units 50,20 separated from one another, and FIG. 5 is a similar view showing a quantity of salt 12 loaded into the bottom unit 20. In at least some embodiments, the two units 20,50 are removably coupled to one another via extra strength magnets 22,52, such as neodymium disc magnets or the like, that are disposed at or near the surface of one or both units 20,50 of the device 10. (In the illustrated embodiment, the magnets 22,52 are located inside the respective units 20,50 but are shown in broken lines.) Furthermore, electrical connections are created between internal electrical components of the two units 20,50 via electrical contacts 24,54, which may be spring-loaded contacts disposed on corresponding surface locations of the two units 20,50. The contacts 24,54 are preferably arranged such that placing the top unit 50 on the bottom unit 20 with the magnets 22,52 aligned causes the electrical contacts 24,54 to make contact with each other so long as the top unit 50 remains in place on the bottom unit 20. In some embodiments, magnetic contacts may be utilized.

Figure 6:
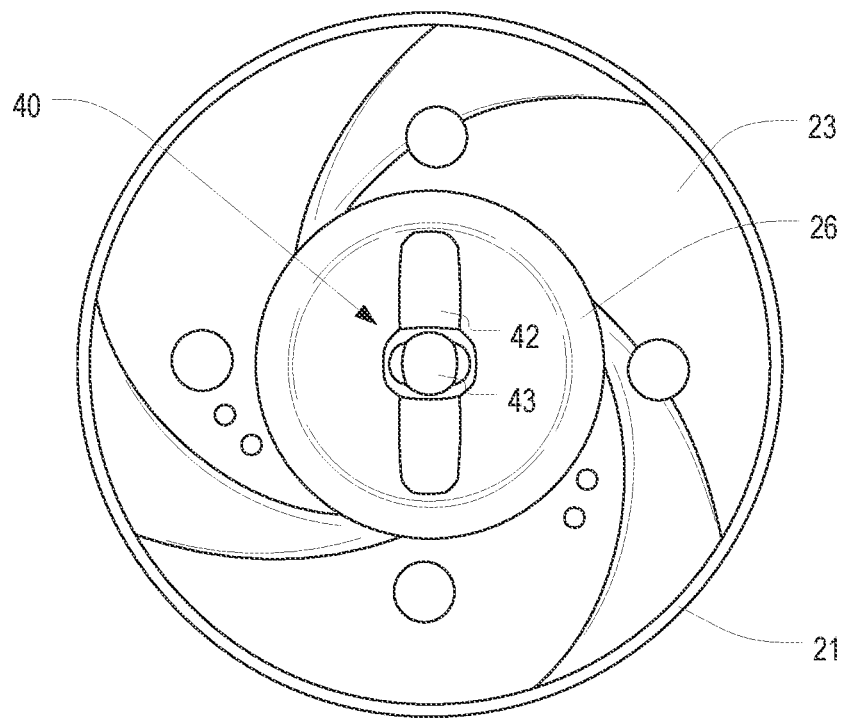
FIG. 6 is a top view of the bottom unit of the halotherapy device of FIG. 4.
Figure 8:
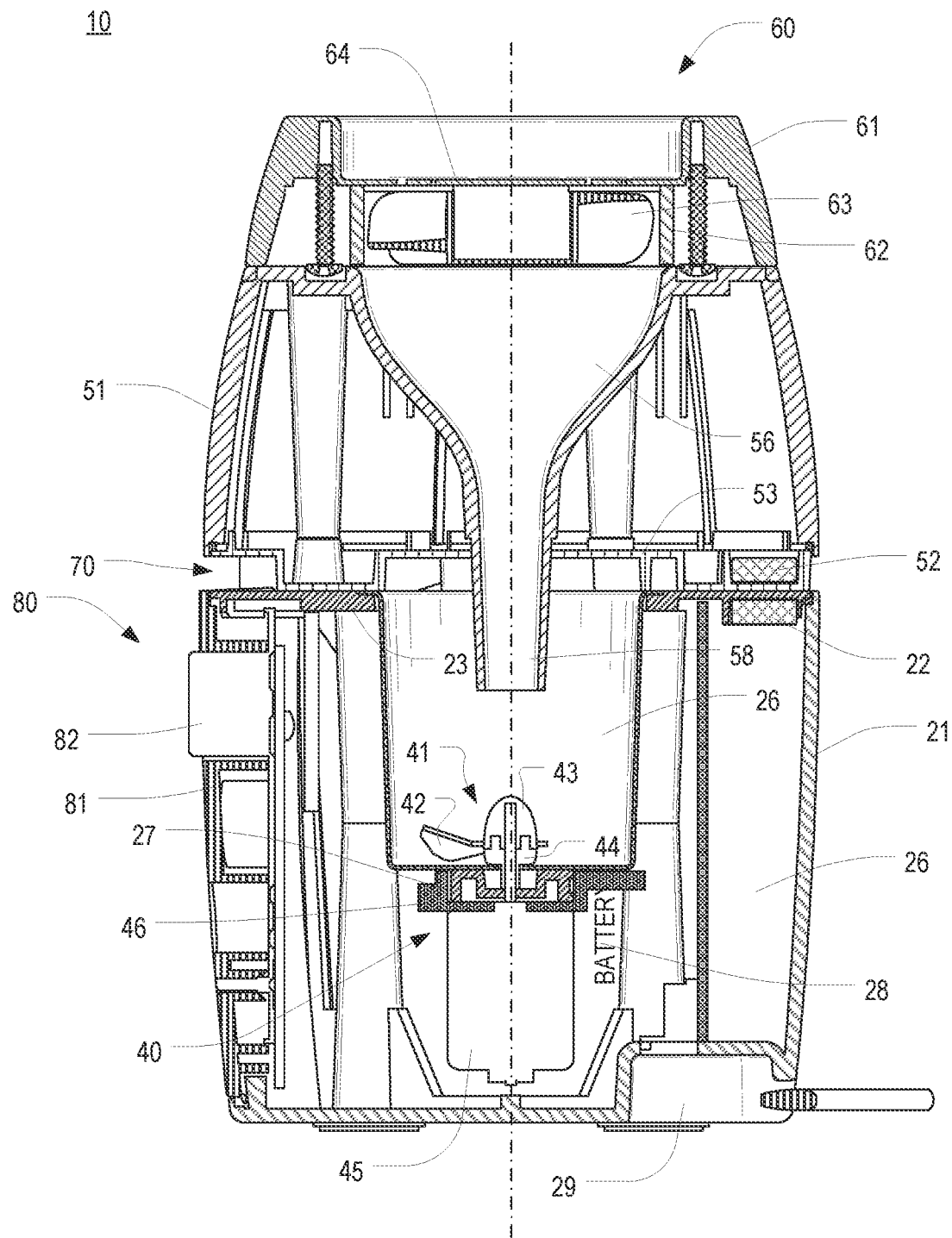
FIG. 8 is a right side cross-sectional view of the halotherapy device of FIG. 2, taken along line 8-8, with various elements thereof not included for clarity.

FIG. 6 is a top view of the bottom unit 20 of the halotherapy device 10 of FIG. 4, and FIG. 8 is a right side cross-sectional view of the halotherapy device 10 of FIG. 2, taken along line 8-8, with various elements thereof not included for clarity. The bottom unit 20 includes a salt grinding chamber 26, a grinder 40, a user interface 80, and an electrical subsystem including a battery 28, power supply 29 and charging circuit (not shown), all carried in a first housing 21. The housing 21 is preferably plastic and may be unitary or may be comprised of a plurality of separate housing components. A top wall 23 of the housing 21 includes a central opening in which the salt grinding chamber 26 is carried. The top wall 23 or other portion of the housing 21 may incorporate a basket 27 or other structural member to support the grinding chamber 26. The salt grinding chamber 26 is open to the top and includes cylindrical side walls and a closed bottom, although in other preferred embodiments a different geometric shape may be used, such as a cone or portion thereof, a partially cylindrical/partially cone-like shape, or the like, so long as the horizontal cross-section is substantially circular along most or all of its height. The salt grinding chamber 26 receives salt 12 for pulverization, as further described below, and is preferably made of metal that is resistant to corrosion or other damage from the effects of salt and is hard enough to withstand repeated impacts from small pieces of salt.

Figure 7A:
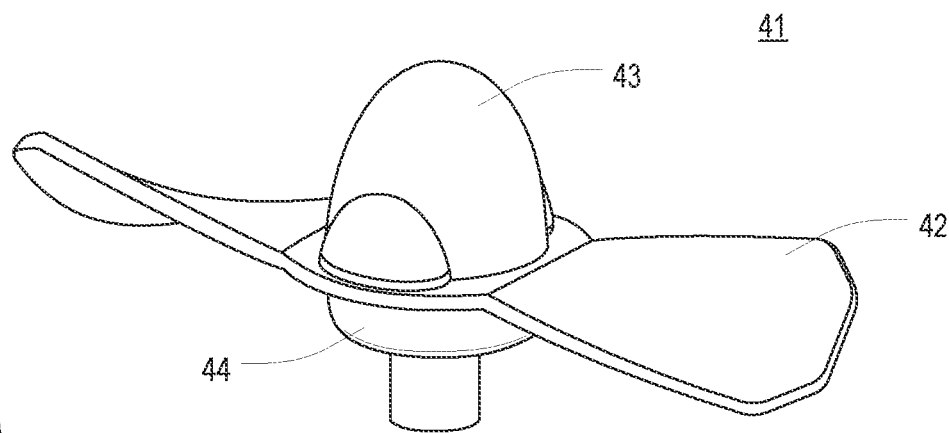
FIG. 7A is a perspective view of the blade assembly of FIG. 6.
Figure 7B:
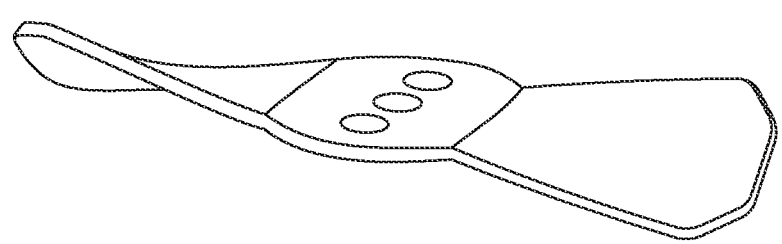
FIG. 7B is a perspective view of the blade of FIG. 7A, shown in isolation.

The grinder 40 includes a high-speed pulverizing fan 41 driven by a motor 45 supported in the housing 21 by a motor mount (not shown). In at least some embodiments, vibration dampening 46 is provided between the motor 45 and the grinding chamber 26. FIG. 7A is a perspective view of the portions of the pulverizing fan 41 of FIG. 6, and FIG. 7B is a perspective view of the blade of FIG. 7A, shown in isolation. The rotating blade assembly 41 includes a spacer or shaft adapter 44 mounted at the upper end of the motor spindle, a grinding blade 42 mounted on the spacer 44, and a cap 43. The pulverizing fan 41 is disposed at the bottom of the grinding chamber 26 such that the blade 42 is arranged to rotate coaxially relative to the cylindrical walls of the barrel 26. The blade 42 is rotated at a high speed such that granular salt contained in the barrel 26 is driven around the interior thereof, impacting against the blade 42 and the side walls of the barrel 26 and gradually being broken into smaller and smaller pieces. Preferably, the blade 42 is driven at a rotational speed of at least 5000 rpm, and more preferably the blade 42 is driven at a rotational speed of at least 7500 rpm. In at least some embodiments, the blade 42 is driven at a rotational speed of approximately 8700 rpm. Notably, the vanes or fins of the grinding blade 42, of which there are two in the illustrated embodiment, are angled in such a way that when rotated during normal operation they push air toward the bottom of the chamber 26. Thus, the high speed rotational movement of the blade 42 not only impinges on the granular salt as it rotates, causing it to break apart into ever-smaller pieces, but it also creates a downdraft that pulls air downward and helps move the salt 12 within the barrel 26 as further described below.

The bottom unit 20 includes a salt grinding chamber 26, a grinder 40, a user interface 80, and an electrical subsystem including a battery 28, power supply 29 and charging circuit (not shown), all carried in a first housing 21. The housing 21 is preferably plastic and may be unitary or may be comprised of a plurality of separate housing components. A top wall 23 of the housing 21 includes a central opening in which the salt grinding chamber 26 is carried.

Referring again to FIG. 8, the top unit 50 includes a funnel-shaped conduit 56 and an exhaust unit 60 carried in a second housing 51. The exhaust unit 60 includes a high-speed fan unit 62 and a salt aerosol exhaust grille 64 that may be carried in their own housing 61. The primary top unit housing 51 and the exhaust unit housing 61 are preferably produced from the same plastic as the bottom unit housing 21 and may each be unitary or may be comprised of a plurality of separate housing components. The horizontal cross-section of the funnel-shaped conduit, which may be integral with the top unit housing 51, is preferably circular throughout and is coaxial with the salt grinding chamber 26 and the axis of rotation of the grinding blade 42. The funnel-shaped conduit 56 includes a central stem 58 that penetrates a bottom wall 53 of the housing 51 and extends downward into the grinding chamber 26. In at least some embodiments, the stem 58 extends a distance of at least 20% of the interior height of the grinding chamber 26, and preferably the stem 58 extends a distance of at least 33% of the interior height of the grinding chamber 26.

The fan unit 62 is disposed in the wide end of the funnel-shaped conduit, with the exhaust grille 64 disposed on the outlet side (above) of the fan unit 62. The fan unit 62 is preferably attached to the underside of the exhaust grille 64, which may be integral with the exhaust unit housing 61. The fan 63 is arranged such that it is generally coaxial with the stem 58 of the conduit 56. The opening at the wide end of the conduit 56 is fitted closely, and in some embodiments sealed, around the inlet to the fan 63 such that rotation of the fan 63 tends to draw air up through the stem 58 of the conduit 56, through the wide end of the conduit 56, through the fan unit 62, and out through the exhaust grille 64. Preferably, the fan 63 is driven at a rotational speed of at least 2500 rpm, and more preferably the fan 63 is driven at a rotational speed of at least 4000 rpm. In at least some embodiments, the fan 63 is driven at a rotational speed of approximately 5000 rpm. An example of an exhaust fan unit 62 suitable for use in one or more preferred embodiments of the present invention is the Sunon Model MF60151VX-1000UA99 fan. The fan unit 62 is powered by the electrical subsystem of the bottom unit 20, including the battery 28, power supply 29, and charging circuit, with connections being made via spring-loaded contacts, magnetic contacts, or the like. The entire fan unit 62 is preferably separable from the top of the top unit 50 to permit the funnel conduit 56 and fan unit 62 to be cleaned and serviced. In at least some embodiments, the two units are removably coupled to one another via magnets, with the electrical contacts for the fan unit 62 being connected and maintained when the fan unit 62 is placed on the bottom unit 50 with the magnets aligned.

Figure 9:
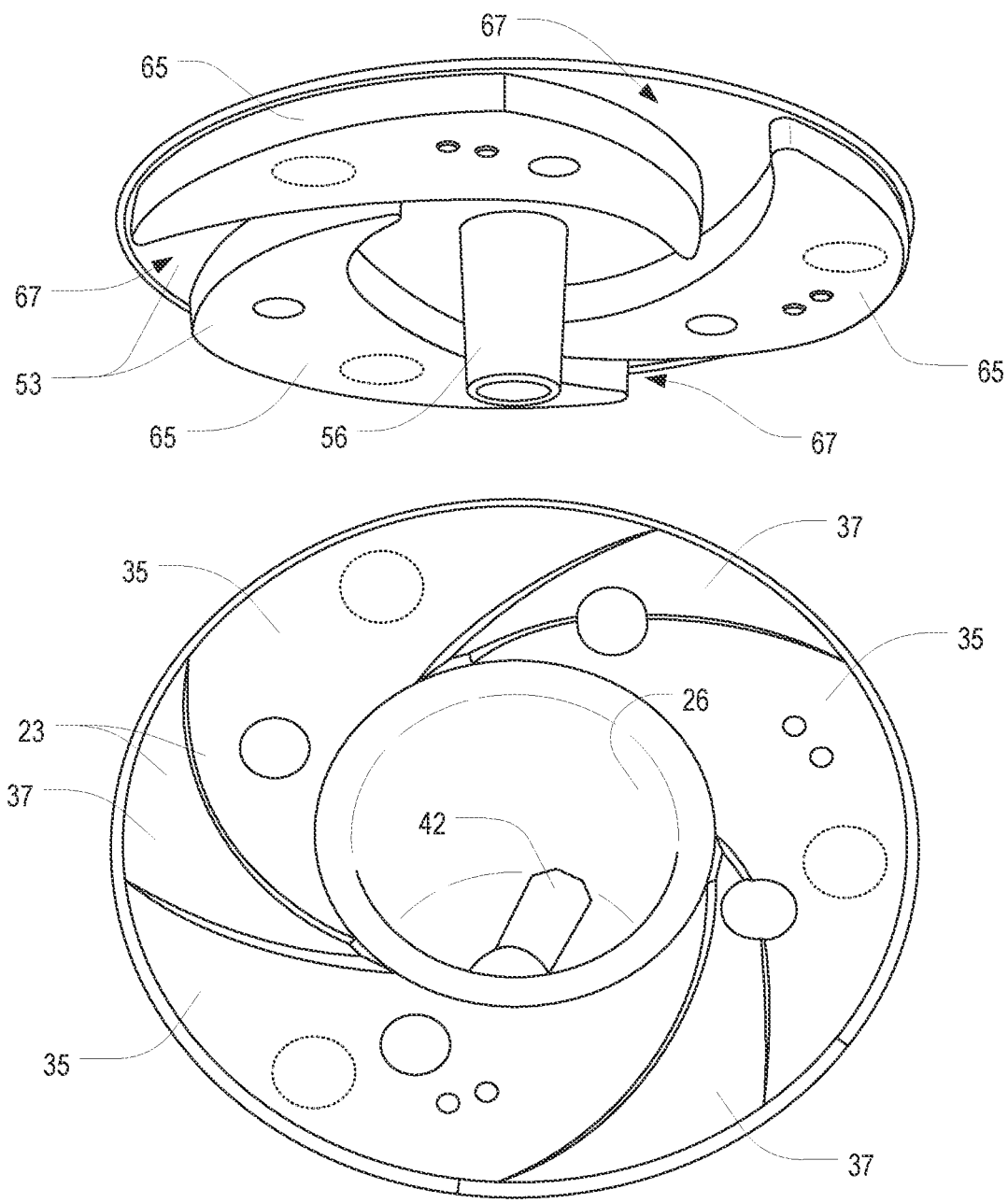
FIG. 9 is an enlarged perspective view of portions of the separated halotherapy device of FIG. 4 illustrating the surfaces used to form the air intake assembly.

As noted previously, an air intake assembly 70 is arranged at the junction between the top unit 50 and the bottom unit 20. In some embodiments, an air intake assembly may be an independent structure, but in various preferred embodiments, the air intake assembly 70 is defined by various surfaces on the bottom wall 53 of the top unit 50 and the top wall 23 of the bottom unit 20. In this regard, FIG. 9 is an enlarged perspective view of portions of the separated halotherapy device 10 of FIG. 4 illustrating the surfaces used to form the air intake assembly 70. As perhaps best shown therein, the bottom wall 53 of the top unit 50 and the top wall 23 of the bottom unit 20 include complementary baffle structures and surfaces which together form the walls of three air ducts 72. In particular, the bottom wall 53 of the top unit 50 includes three roughly crescent-shaped structural bodies 65 descending therefrom, while the top wall 23 of the bottom unit 20 includes three corresponding surface areas 35 of complementary shape that receive the structural bodies 65 when the top unit 50 is installed on the bottom unit 20. Similarly, three inlet gaps 67 between the structural bodies 65 align with three corresponding inlet surfaces 37 on the bottom unit 20. Together, three air ducts 72 extending from the periphery of the device 10 to the center of the device are thus defined. Two of these ducts 72 are illustrated, for example, in FIGS. 1-3.

In the illustrated embodiment, the ceiling and side walls of each air duct 72 are defined by baffle surfaces and structures of the bottom wall 53 on the top unit 50, while the floor of each air duct 72 is defined by surfaces and structures of the top wall 23 on the bottom unit 20. Notably, however, the ducts may be formed in different ways, including defining the side walls of each duct using baffle surfaces and structures of the bottom unit, or in some cases defining the entirety of each duct in either the top unit or the bottom unit. Also, although three air ducts 72 are shown, in some embodiments the number of ducts could be increased or decreased.

The shape of each air duct 72 is significant in a variety of ways. First, the width of each duct 72 narrows significantly as it nears the center of the device 10 and empties into the top of the chamber 26. Second, the height of each duct 72 narrows slightly as it nears the center of the device 10. In the illustrated embodiment, this is accomplished by ramping the floors of the ducts 72 slightly upward. Third, and perhaps most significantly, each duct 72 takes the form of a spiral arm tapering from a wide inlet to a much narrower outlet that empties into the top of the grinding chamber 26. The spiral arms are arranged to spiral out from an axis that is coaxial with the funnel-shaped conduit 56, the grinding chamber 26, and the axis of rotation of the blade 42. Furthermore, the spiral arms are arranged such they spiral inward in the same rotational direction as that of the rotating blade, which in normal operation is counter-clockwise when viewed from above. Rotation of the blade 42 at the bottom of the chamber 26 tends to draw air in through the ducts, and because those ducts spiral inward in the same rotational direction as that of the rotating blade 42, and narrow as they near the center, the air being drawn in is accelerated more quickly in the direction of rotation. As further described below, each of these features helps create a desired air pattern into the grinding chamber 26 and from there up onto the funnel conduit 56. In some embodiments, one or more of these features may be omitted so long as a reasonable facsimile of the desired air pattern is still created, but it is believed that all of them together are particularly useful in creating such air pattern.

Figure 10:
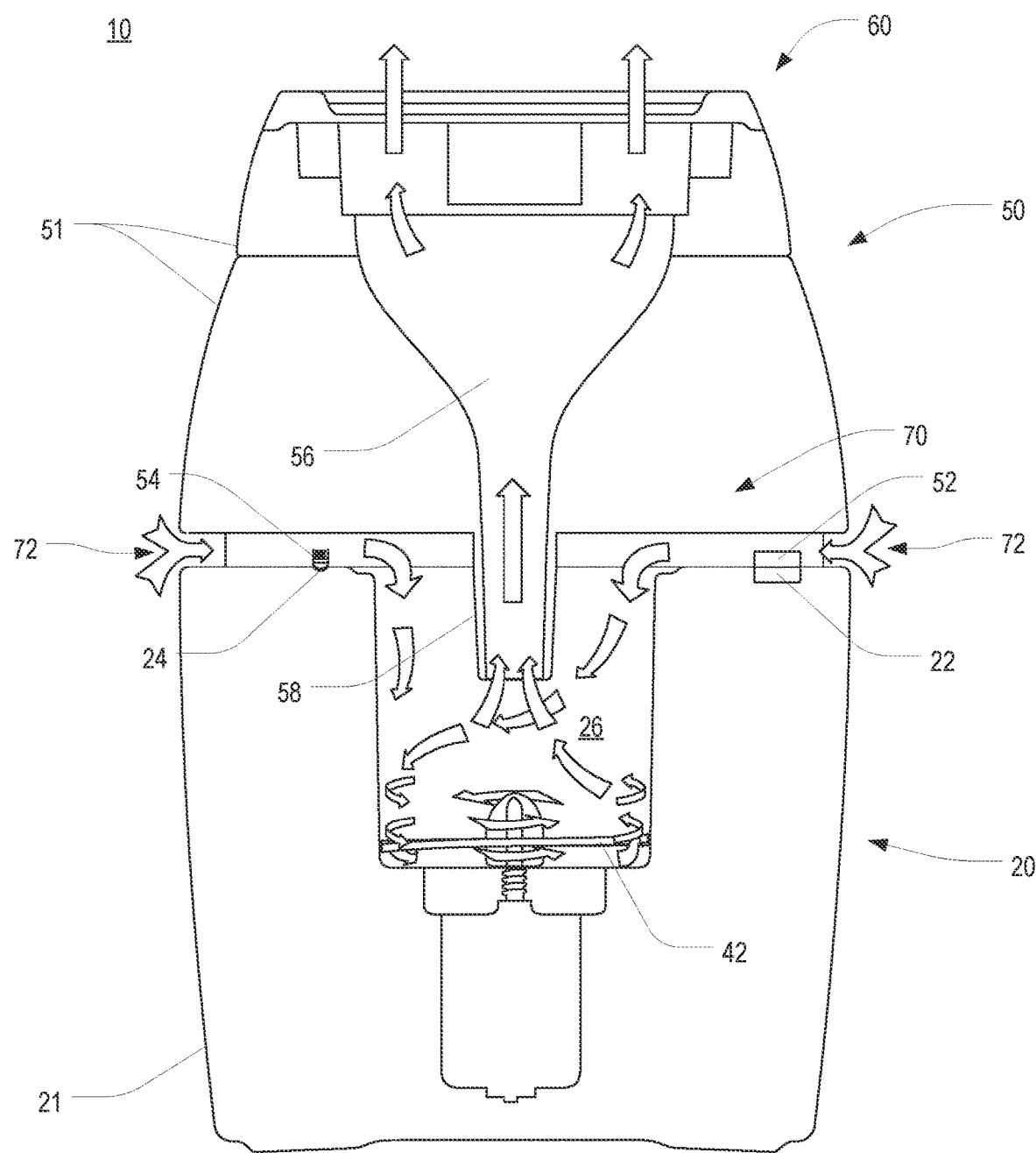
FIG. 10 is a partially schematic side cross-sectional view of the halotherapy device of FIG. 8.
Figure 11:
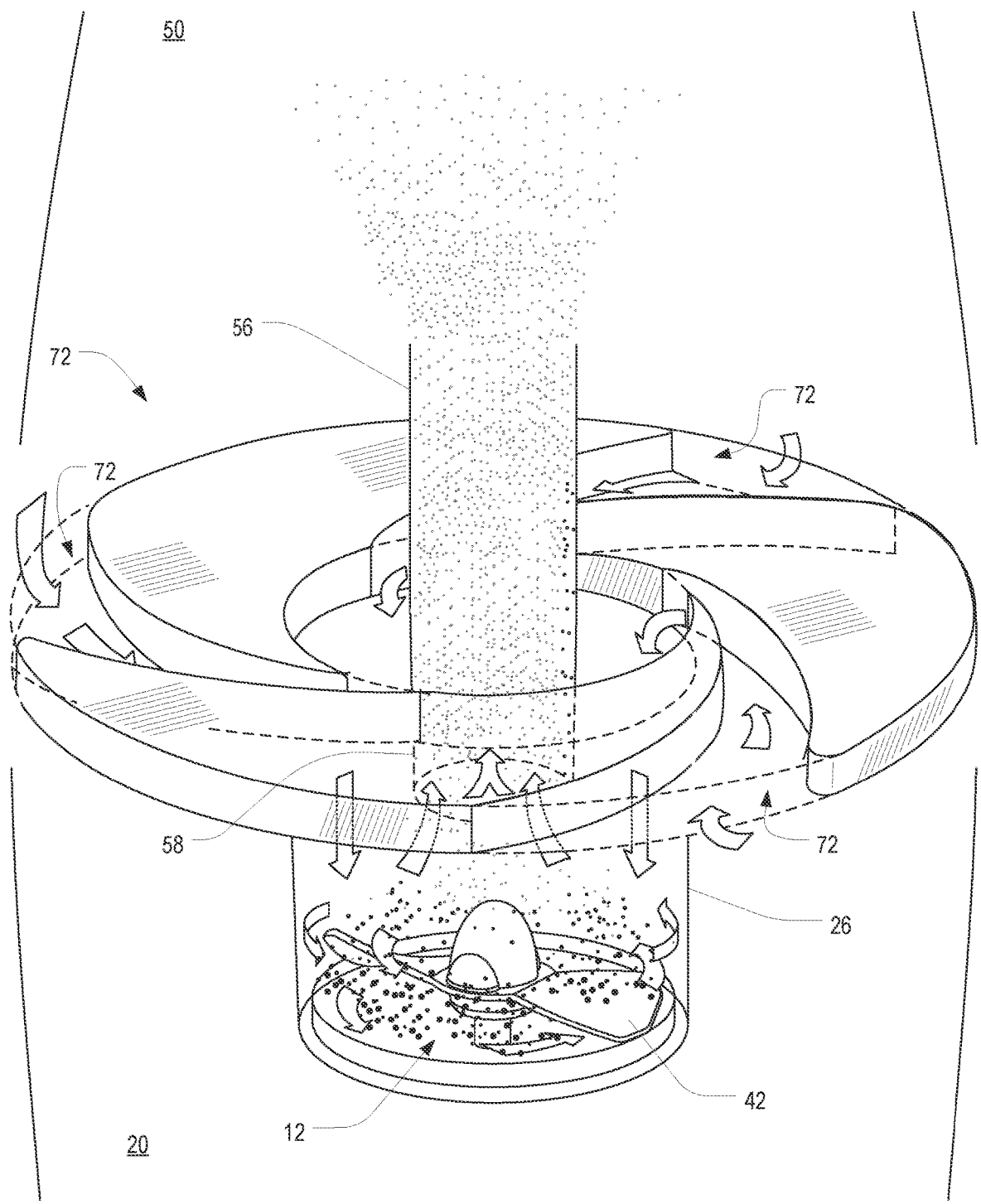
FIG. 11 is a partially schematic perspective view of interior portions of the halotherapy device illustrating the flow of air and salt aerosol through the device.

As referenced previously, the arrangement and configuration of the ducts 72, grinding chamber 26, grinding blade 42, funnel conduit 56, and upper fan 63 all contribute to a particular desired air pattern which, when applied to an appropriate quantity of salt loaded into the grinding chamber 26, causes salt aerosol to be produced and exhausted into the room. The device 10 produces the desired salt aerosol using a pulverizing stage, filtering stage, and a distribution stage. In this regard, FIG. 10 is a partially schematic side cross-sectional view of the halotherapy device 10 of FIG. 8, while FIG. 11 is a partially schematic perspective view of interior portions of the halotherapy device 10 illustrating the flow of air and salt aerosol through the device 10. The air flow itself is illustrated in FIG. 10. Ambient air is brought in through the air ducts 72 by the force of air currents generated by the counterclockwise rotation of the grinding blade 42. As the air passes through the narrowed ducts it accelerates, and the rotational swirl of the ducts 72 helps direct the air into a swirling pattern around the walls of the barrel 26 immediately upon entering the barrel 26. At the same time, the fan 63 in the top unit 50 draws air out of the barrel 26 and up through the funnel conduit 56 before passing through the fan unit 62 and out through the exhaust grille 64. This causes an updraft toward the center of the grinding chamber 26 at the same time that a general downdraft exists around the walls of the grinding chamber 26. Notably, the funnel shape of the conduit 56 not only controls the precise location of the updraft in the barrel 26 but also tends to create an even higher flowrate through the stem 58 of the funnel 56 than through the top thereof. This, coupled with the high speed of the upper fan 63 creates a very powerful current in the center of barrel 26 while allowing the downdraft around the periphery. Overall, by using a high-speed grinding blade 42 in combination with a high speed exhaust fan unit 62, the aerosolized salt is preferably moved at a rate of at least 10 cfm, and more preferably at a rate of at least 20 cfm. In at least some embodiments, the aerosolized salt is moved at a rate of approximately 25 to 30 cfm.

The applicability of this air flow to a quantity of granular salt is illustrated in FIG. 11. As with FIG. 10, air is shown entering through the spiral ducts 72 and flowing downward along the periphery of the grinding chamber 26. Granular salt 12 loaded in the barrel 26 is spun around by the motion of the grinding blade 42, first due to collisions with the blade 42 and then also by air currents generated in the barrel 26. In this pulverizing stage, the salt 12 quickly and efficiently begins to break apart into smaller and smaller pieces, both through collisions with the blade 42 and through collisions with the walls of the barrel 26. Initially, the weight of each piece of salt 12 keeps it near the bottom of the barrel 26, where it continues to be ground down into very small particles. Eventually, however, the pieces become light enough, particularly relative to their surface area, that they tend to waft about on the circular air currents until caught up in the updraft in the center of the barrel 26. The salt particles that ultimately escape are preferably no larger than 12 microns to 15 microns in diameter, are preferably less than about 10 microns in diameter, and most preferably include a high percentage of particles that are less than about 5 microns in diameter. As shown in FIG. 11, these very small salt particles are then carried up through the funnel conduit 56, where it may be exhausted by the fan unit 62. Notably, the tangential inlet flow of air into the top of the grinding chamber 26 also helps prevent the very small salt particles from escaping through the ducts 72.

The air pattern thus produced has the effect of filtering the salt particles 12 by size. The filtering stage occurs more or less simultaneously with the pulverizing stage and filters the salt particles using the geometry of the grinding chamber 26 as well as the principle of varying drag on small and large particles. The air ducts 72 draw the air into the top of the grinding chamber 26 along paths that are tangential to the circular opening at the top of the chamber 26 in the same direction as the rotation of the pulverizing blade 42. As the salt spins around the chamber 26, the smallest particles slow down due to a decrease in drag, which correlates directly with a decrease in the particle diameter. As each particle's velocity decreases it is influenced by the air current flowing towards the funnel stem 58, which serves as the chamber outlet, and migrates toward the center of the chamber 26. Notably, the inlet to the stem 58 of the funnel conduit 56 is located well below the air ducts 72, thereby serving to position the updraft current at a location well down into the chamber 26 to collect the fine salt particles. This multi-part flow design naturally filters the salt particles 12, releasing the smaller particles for flow through the distribution stage of the device 10, in which the aerosolized salt particles flow through the funnel conduit 56 for discharge to the atmosphere through the exhaust unit 60. In particular, the filtering stage is designed to aerosolize salt by taking in particles of salt, preferably USP pharmaceutical grade salt that begins as particles that are approximately 0.1 to 1.0 mm in diameter, and emitting a fine salt aerosol wherein at least 80% of the emitted particles are 5 microns or less in diameter.

Electronic operation of the device 10 is controlled by the electrical subsystem in view of input from the user interface 80. In the illustrated embodiment, the user interface 80 primarily includes a start or power button 82 and an indicator light 83, all set in a user interface panel 81. In this embodiment, preferred for its simplicity and avoidance of complications associated with different use modes, a user needs only to load the device 10 and press the button, with operation of the device 10 then continuing for a predefined period of time and then ending. As described further below, however, other embodiments may provide different use modes and may involve more complicated user interfaces.

In at least some commercial embodiments, the device 10 is intended to be used with prepackaged single-use/single-dose quantities of salt. In at least some such embodiments, each dose is between 5 and 10 grams of salt, and it has been determined experimentally that best effects may be achieved with a dose size of about 6 grams. The top unit 50 is removed from the bottom unit 20, a package is opened and emptied into the grinding chamber 26, and the top unit 50 is replaced on the bottom unit 20 with the magnets 22,52 aligned with each other. Once the user presses the start button 82, the grinder 40 and exhaust unit 60 operate for a predetermined period of time to grind the granular salt 12 into a salt aerosol. The predetermined operational period is preferably between about 5 and 30 minutes, and more preferably between about 10 and 20 minutes inclusive. During this time and for a period of time thereafter, anyone in the vicinity of the device 10 may then receive a salt therapy session.

In at least some embodiments, the grinder 40 and exhaust unit 60 operate separately from each other, with operation of one or both being discontinuous during the overall operational period. For example, in at least some commercial embodiments, the grinder 40 is programmed to operate intermittently during the operational period of the device 10, while the exhaust unit 60 operates continuously.

Notably, density of the salt aerosol that is produced, and thus the effects of the session, are dependent on the size of the area where the device 10 is used. An enclosed environment holds the salt aerosol and allows the user to have a longer session. In some methods of use, the device 10 is operated using the aforementioned dose size for the predetermined period of time in an enclosed space that is from about 125 cu. feet (approximately 4×4×8) to 500 cu. feet (approximately 6×8×10).

After the session is ended, the device 10 should generally be cleaned. The top and bottom units 50,20 may be separated, and the exhaust unit 60 may be removed from the top unit 50. In at least some embodiments, the various components may be brushed to remove all salt residue from the surfaces thereof. It is important for each session to begin with a clean grinding chamber 26, clean funnel conduit 56, and a fresh dose of salt 12.

Figure 12:
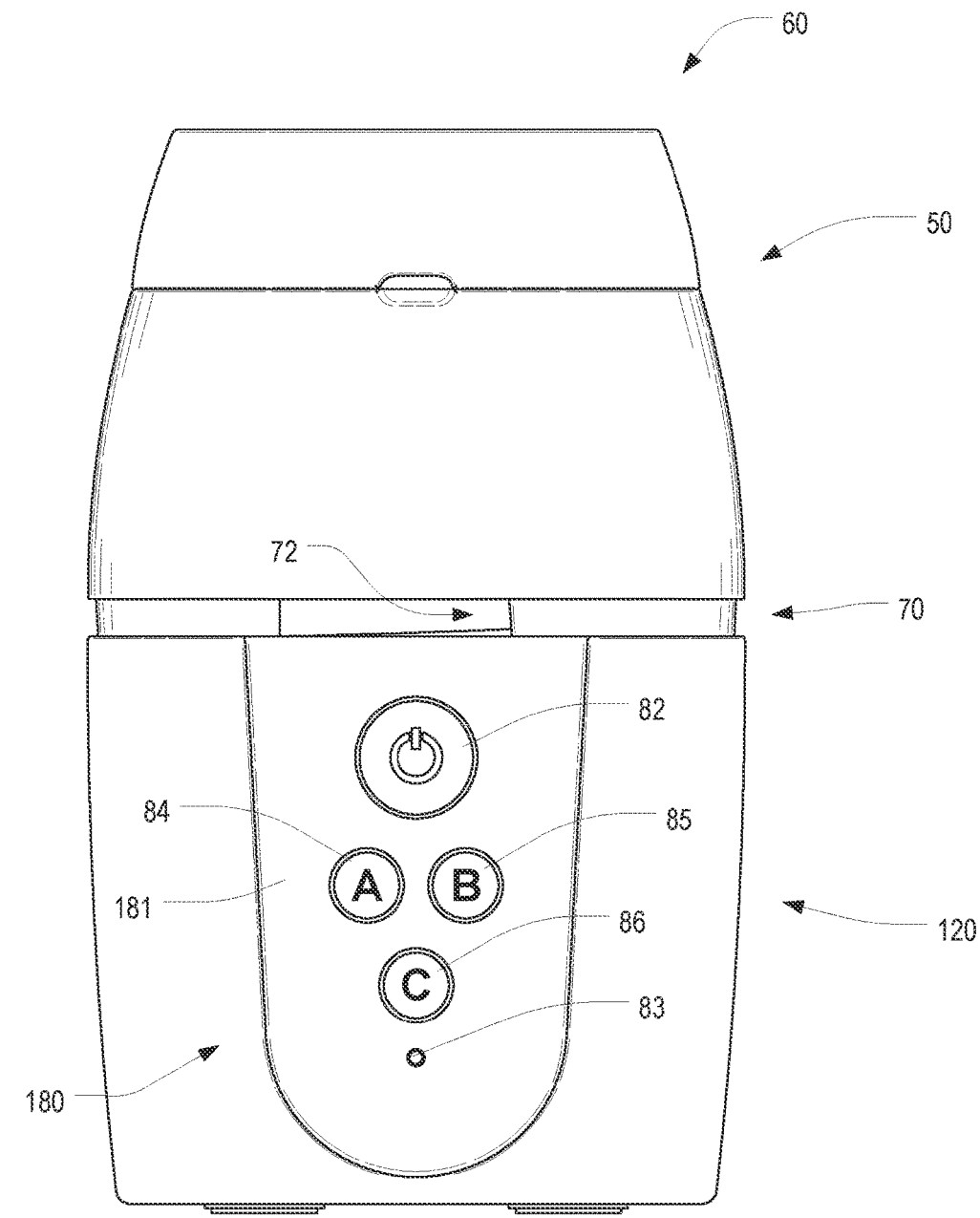
FIG. 12 is a front view of a compact halotherapy device in accordance with one or more further preferred embodiments of the present invention.

FIG. 12 is a front view of a compact halotherapy device 110 in accordance with one or more further preferred embodiments of the present invention. The device 110 of FIG. 12 is similar to the device 10 of FIG. 1, with the top and bottom units 50,120 identical or nearly identical to those of the first device 10, but includes a more sophisticated user interface 180 and includes additional operational modes. More particularly, the user interface 180 of the device 110 of FIG. 12 includes not only a start or power button 82 and an indicator light 83 but three mode selector buttons 84,85,86, all set in a user interface panel 181. This device 110 is operated by selecting one of the three modes A, B, C using the respective mode selector button 84,85,86, and the start button 82 is pressed to start operation in that mode. For example, in operational mode A, the device 110 has an overall operational period of 10 minutes but with the grinder 40 only operating intermittently; in operational mode B, the device 110 has an overall operational period of 20 minutes but with the grinder 40 only operating intermittently; and in operational mode C, the device 110 has an overall operational period of only 5 minutes but with the grinder 40 operating continuously. In various embodiments, the intermittent operation of the grinder 40 may be adjusted to change the length of the intermittent periods, the length of time between the intermittent periods, or the like. Providing multiple operational modes advantageously allows the device 110 to be used for different types of sessions. For example, operational mode A, which produces the mildest salt aerosol concentration, may be best suited for asthmatics and children under 6; operational mode B, which produces a higher salt aerosol concentration and/or operates for a longer period of time, may be best suited for general all-around sessions for those suffering from COPD, allergies, colds, flus, bronchitis, coughs, or eczema, and for athletes wishing to increase oxygenation or clear their lungs; and operational mode, which produces the highest salt aerosol concentration, may be best suited for outdoor or large-room use. It will also be appreciated that a user may need to experiment with the desired operational mode, starting with operational mode A and proceeding from there.

Figure 13:
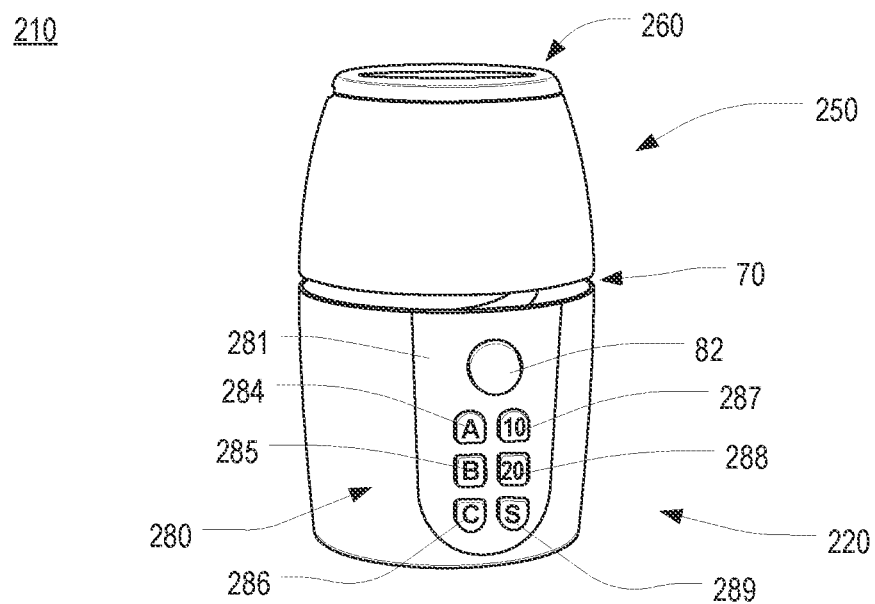
FIG. 13 is a front perspective view of a compact halotherapy device in accordance with one or more still further preferred embodiments of the present invention.
Figure 14:
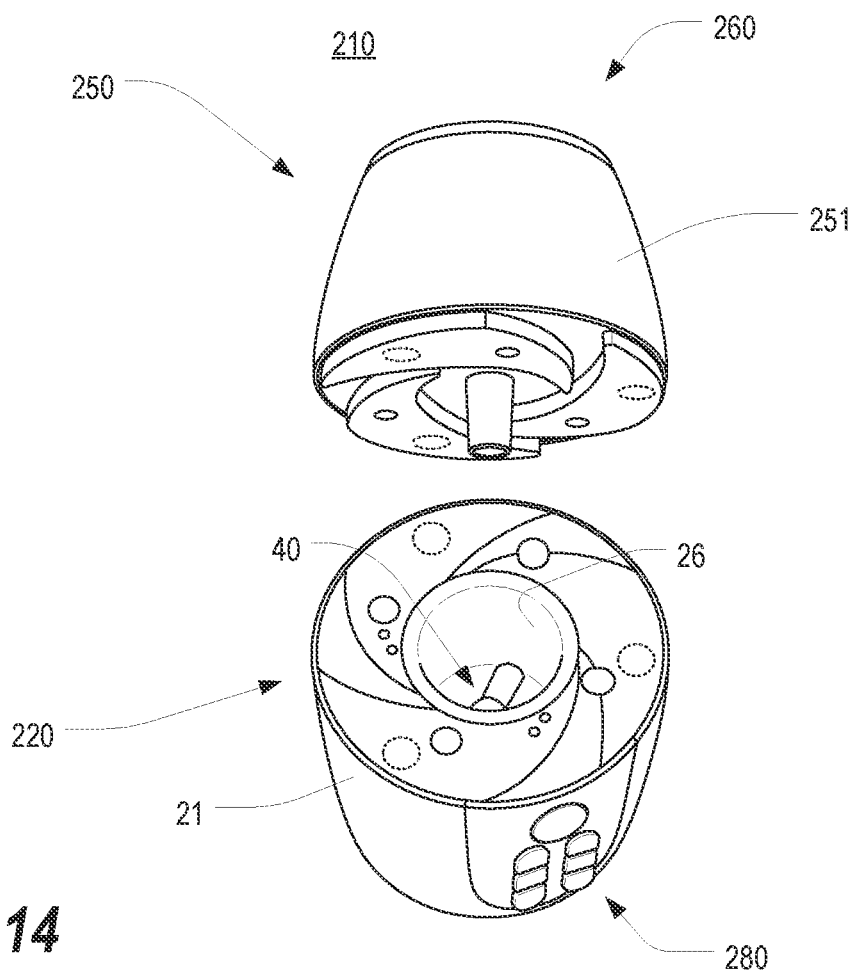
FIG. 14 is a perspective view of the halotherapy device of FIG. 13, shown with the top and bottom units separated from one another.
Figure 15:
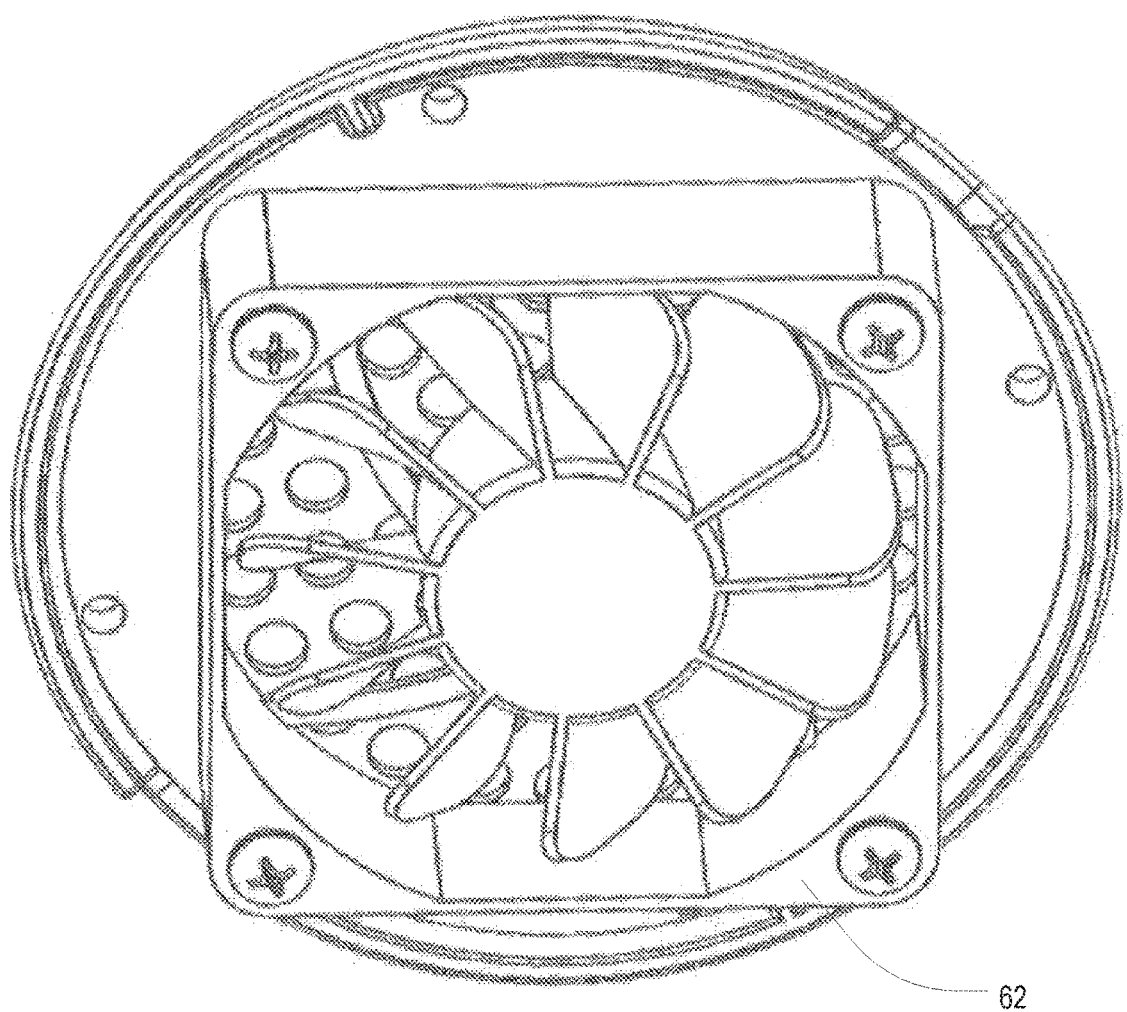
FIG. 15 is a bottom perspective view of the exhaust unit of the halotherapy device of FIGS. 13 and 14.

FIG. 13 is a front perspective view of a compact halotherapy device 210 in accordance with one or more still further preferred embodiments of the present invention, and FIG. 14 is a perspective view of the halotherapy device 210 of FIG. 13, shown with the top and bottom units 250,220 separated from one another. The device 210 of FIGS. 13 and 14 is fairly similar to the device 110 of FIG. 12, but with at least two differences. First, the bottom unit 220, although identical or nearly identical to the bottom unit 120 of FIG. 12, includes a more sophisticated user interface 280 and includes additional operational modes. Second, the top unit 250 and its exhaust unit 260 each have a different form factor than that of the corresponding component in the device 110 of FIG. 12. More particularly, the exhaust unit 260 is installed more predominantly within the top of the top unit 250, rather than being predominantly installed on top of the top unit 50, and is connected to the rest of the top unit 250 via direct electrical wires (not shown) rather than via spring-loaded or magnetic electric contacts. In this regard, FIG. 15 is a bottom perspective view of the exhaust unit 260 of the halotherapy device 210 of FIGS. 13 and 14.

The user interface 280 of the device 210 of FIG. 13 includes a start or power button 82, three mode selector buttons 284,285,286, and three operational period buttons 287,288,289 all set in a user interface panel 281. The operational modes of the device 210 of FIG. 13 may be somewhat similar to those of the device 110 of FIG. 12, with three mode selector buttons 284,285,286 being used to select between three primary operational modes, but the operational period buttons 287,288,289 allow the user to select an overall operational time period separately from setting the operational mode. For example, when using operational mode A, which produces the lowest concentration of salt aerosol, the user may choose to set an overall operational period of 10 minutes or 20 minutes using the 10-minute or 20-minute operational period buttons 287,288, respectively. In at least some embodiments, operational mode C may only be utilized with the continuous or steady "S" operational period, which is limited to, for example, 5 minutes. In this device 210, the user selects both the mode and the operational period before pressing the start button 282 to initiate operation.

Advantageously, devices in accordance with various preferred embodiments of the present invention provide efficient salt aerosolizing for halotherapy in a very compact package that is readily portable and can operate via rechargeable battery in nearly any setting, thus providing considerable flexibility to a user. In at least some embodiments, the overall size of such a device is about 12 inches high with a diameter of about 5 inches. Such devices also enable users to carry out halotherapy sessions of just a few minutes in length, or of lengths including 10 and/or 20 minutes, thereby providing greater flexibility to the user than the lengthy sessions commonly administered prior to introduction of this device.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claim(s) appended hereto and the equivalents thereof.

What is claimed is:

1. A portable halotherapy device, comprising:
    (a) one or more housings that may be coupled together to define a single operational unit;
    (b) a grinding chamber, having an interior with a moving grinding blade therein, that is disposed within the one or more housings and that breaks apart dry granular salt in the interior thereof into salt particles small enough to be used for halotherapy;
    (c) an air intake assembly, including one or more air ducts that each route ambient air from outside the one or more housings into the interior of the grinding chamber;
    (d) a fluid conduit that is disposed within the one or more housings and that has an inlet at a first end and an outlet at a second end, wherein the conduit extends upward from the first end, wherein the inlet is in fluid communication with the interior of the grinding chamber; and
    (e) an exhaust unit, the exhaust unit including a high-speed fan disposed within the one or more housings at the second end of the fluid conduit and in communication with the outlet thereof;
    (f) wherein the moving grinding blade and the high-speed fan together operate to produce an airflow pattern that causes ambient air to be brought through the air ducts of the air intake assembly and into the grinding chamber where a regular and predictable first air current is produced, wherein the airflow pattern further causes air to divert from the first air current upward, in a second air current, into the inlet of the fluid conduit and through the high-speed fan of the exhaust unit for distribution to the outside of the one or more housings; and
    (g) wherein the first air current assists in moving the dry granular salt around the grinding chamber and against surfaces thereof, thereby assisting in breaking apart the dry granular salt into small salt particles for halotherapy, while the second air current is arranged relative to the first air current such that the small salt particles, but not larger pieces of salt, are carried in the form of a salt aerosol by the second air current upward into the inlet of the fluid conduit and through the high-speed fan of the exhaust unit for distribution to the outside of the one or more housings, thereby facilitating a halotherapy session.

2. The portable halotherapy device of claim 1, wherein the one or more housings include a bottom unit and a top unit, wherein the grinding chamber is disposed in the bottom unit, and wherein the exhaust unit is disposed at the top of the top unit.

3. The portable halotherapy device of claim 2, wherein the top unit is removably coupled to the bottom unit.

4. The portable halotherapy device of claim 2, wherein the exhaust unit includes a separate housing that is removably coupled to the top of the top unit.

5. The portable halotherapy device of claim 1, wherein the first end of the fluid conduit extends downward into the interior of the grinding chamber.

6. The portable halotherapy device of claim 5, wherein the fluid conduit is funnel-shaped with the first end thereof being narrow and the second end thereof being substantially wider than the first end.

7. The portable halotherapy device of claim 5, wherein the fluid conduit defines a first axis, and wherein the first axis extends downward through a geometric center of the grinding chamber.

8. The portable halotherapy device of claim 7, wherein the high-speed fan of the exhaust unit rotates around a second axis, and wherein the first and second axes are collinear.

9. The portable halotherapy device of claim 7, wherein the grinding blade rotates around a third axis, and wherein the first and third axes are collinear.

10. The portable halotherapy device of claim 5, wherein the horizontal cross-section of the fluid conduit is circular through its length.

11. The portable halotherapy device of claim 5, wherein the fluid conduit extends into the grinding chamber a distance of at least 20% of the interior height of the grinding chamber.

12. The portable halotherapy device of claim 1, wherein the moving grinding blade is disposed at a bottom of the interior thereof and rotates in a first rotational direction about a first axis.

13. The portable halotherapy device of claim 12, wherein the grinding blade includes one or more downwardly-angled vanes or fins such that the blade pushes air downward and in the first rotational direction as the blade rotates.

14. The portable halotherapy device of claim 1, wherein the first air current flows from outside the one or more housings through the one or more air ducts into the grinding chamber and swirls in a downward and high-speed circular direction around the periphery thereof where the first air current interacts with the dry granular salt and the salt particles as such particles are created, and wherein the second air current flows directly upward at or near a geometric center of the grinding cylinder and into the inlet of the fluid conduit, carrying the resulting salt aerosol up through the fluid conduit and through the high speed fan for distribution to the outside.

15. The portable halotherapy device of claim 14, further comprising an electrical subsystem that operates the fan in the exhaust unit independently from the grinding blade.

16. The portable halotherapy device of claim 1, wherein the small particles are substantially all less than 15 microns in diameter.

17. The portable halotherapy device of claim 16, wherein the small particles are substantially all less than 10 microns in diameter.

18. The portable halotherapy device of claim 1, wherein the small salt particles are carried via the second air current at a rate of at least 10 cfm.

19. The method of claim 18, wherein the small salt particles are carried via the second air current at a rate of at least 20 cfm.

20. A method of producing and distributing a salt aerosol from a portable halotherapy for a halotherapy session, comprising:

(a) drawing ambient air through an air intake assembly, including one or more air ducts;

(b) routing the ambient air into a grinding chamber having an interior with a moving grinding blade therein;
(c) with the grinding blade, breaking apart dry granular salt contained in the interior thereof into salt particles small enough to be used for halotherapy;
(d) with an exhaust unit, including a high-speed fan, drawing air up into an inlet at a first end of a fluid conduit and through the conduit to a second end where the high-speed fan is located, wherein the conduit extends upward from the first end, wherein the inlet is in fluid communication with the interior of the grinding chamber;
(e) with the moving grinding blade and the high-speed fan together, producing an airflow pattern that causes ambient air to be brought through the air ducts of the air intake assembly and into the grinding chamber where a regular and predictable first air current is produced, and that further causes air to divert from the first air current upward, in a second air current, into the inlet of the fluid conduit and through the high-speed fan;
(f) with the first air current, assisting the grinding blade in moving the dry granular salt around the grinding chamber and against surfaces thereof, thereby assisting in breaking apart the dry granular salt into small salt particles for halotherapy;
(g) with the second air current, carrying the small salt particles, but not larger pieces of salt, are carried in the form of a salt aerosol upward into the inlet of the fluid conduit and through the high-speed fan of the exhaust unit; and
(h) distributing the salt aerosol to an environment, thereby facilitating a halotherapy session.

\* \* \* \* \*